Jan. 5, 1971 C. R. POYNER Plant Pat. 3,013
GLADIOLUS PLANT
Filed Dec. 18, 1968
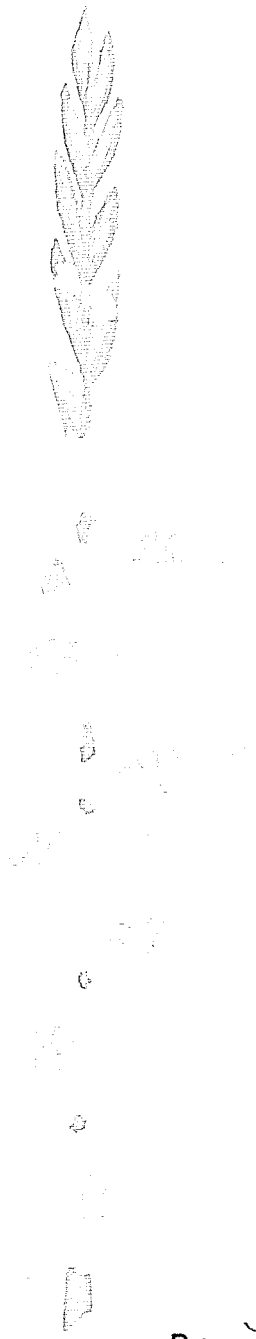
INVENTOR
Claude R. Poyner
By: Lamont Johnston
ATTORNEY

United States Patent Office

Plant Pat. 3,013
Patented Jan. 5, 1971

3,013
GLADIOLUS PLANT

Claude R. Poyner, Jesup, Iowa, assignor to Selected Glads, Inc., New Albany, Ind., a corporation of Tennessee

Filed Dec. 18, 1968, Ser. No. 784,954
Int. Cl. A01h *5/00*

U.S. Cl. Plt.—85 1 Claim

My invention relates to a new and improved variety of gladiolus plant and is notable particularly for its unusual blossom ruffling, beauty of blossom color and ability to perform well in all parts of the United States. I have identified this new variety as seedling #54–1 in my breeding work.

To the best of my knowledge, this variety is a result of a cross between Appleblossom (Plant Pat. No. 1,517) and Party Ruffles (unpatented). Appleblossom was the seed parent and Party Ruffles the pollen parent. Hand-cross pollenization was done by me in a patch on my farm at Jesup, Iowa, but no precaution was taken to prevent a mixture by bees or insects.

This new variety has been asexually reproduced by me in Iowa, by natural increase from cormels through several generations, and its characteristics have proven to be permanently fixed.

The illustration, made a part of this application, shows a single bloom spike, reduced in size. The illustration shows the form and placement of the florets on the spike and is as nearly true to color as it is possible to depict.

In the following detailed description, color plate references are to "The Horticultural Colour Chart," by the British Colour Council. Where there are other references to color, the ordinary dictionary meanings of the terms are intended.

THE PLANT

Growth: Very good, attains a height of 60 inches, overall. Fine propagator.

Blooming: Blooms in 80 days from large bulbs in Iowa.

Stems: Diameter of the stem is ⅝ inch. Color of stem above the bulb is light green.

Foliage: Deep green, rather short and upright growing, making for easy cutting. Leaves are 2 inches across. Plant foliage, excluding the flower spike, is 28 to 30 inches high.

Disease resistance: Very good resistance to known gladiolus diseases.

Corms: Round, plump, smooth, rather high-crowned with good husk covering. Husk has a light tan color. Color of the flash is creamy yellow. Naples Yellow 403/3.

THE FLOWER

Spike: Flowerhead is 30 inches high, with 18 to 20 buds, of which 7 to 8 are open at one time.

Bud:

*Size.*—Opening buds are 2½ inches long.

*Opening.*—Four to five show color at one time.

Flower:

*Arrangement.*—Florets are informally placed on the spike.

*Size.*—Individual florets are 4½ to 5½ inches across.

*Form.*—Ruffled, crimped and somewhat triangular.

*Keeping qualities.*—Very good.

Petals: Ruffled and rounded.

*Size of petals.*—Upper petals are 2½ inches across; lip, 1½ inches.

*Aspect.*—Very heavy substance, with a frosty sheen.

*Fragrance.*—None.

*Color of petals.*—Color is Rose Pink, 427/3.

Reproductive organs: Stamens—A slight cast of orchid on the under side, otherwise white.

Pistil: White.

COMPARISONS

My new variety resembles Appleblossom (Plant Pat. No. 1,517) but differs from it principally as follows:

(1) My variety is deeper and richer in color, and more toward pink.

(2) It has better substance.

(3) It has more ruffling.

(4) It has a frosty sheen.

Having thus discolsed my inveniton, I claim:

1. The new and distinct variety of gladiolus plant, substantially as herein shown and described, characterized by its rugged plant, large size florets, ruffling, heavy substance, and a pink color of blossom having a frosty sheen.

No references cited.

ROBERT E. BAGWILL, Primary Examiner